United States Patent [19]

Babb

[11] 4,381,004
[45] Apr. 26, 1983

[54] EXTRACORPOREAL SYSTEM FOR TREATMENT OF INFECTIOUS AND PARASITIC DISEASES

[75] Inventor: Albert L. Babb, Seattle, Wash.
[73] Assignee: Biomedics, Inc., Arlington Heights, Ill.
[21] Appl. No.: 225,309
[22] Filed: Jan. 15, 1981
[51] Int. Cl.³ ............................................. A61M 1/03
[52] U.S. Cl. ......................... 128/214 R; 128/DIG. 3; 210/638; 210/646
[58] Field of Search ............ 128/214 R, 214 B, 214.2, 128/DIG. 3; 210/434, 438, 638, 646, 651, 927

[56] References Cited

U.S. PATENT DOCUMENTS

| | | | |
|---|---|---|---|
| 3,682,172 | 8/1972 | Freedman et al. | 128/214 B |
| 3,730,835 | 5/1973 | Leeper et al. | 128/214.2 |
| 3,888,250 | 6/1975 | Hill | 128/214 R |
| 3,959,128 | 5/1976 | Harris | 128/214 R |
| 3,963,613 | 6/1976 | Chibata et al. | 128/214 R |
| 4,013,564 | 3/1977 | Nose | 210/434 |
| 4,061,141 | 12/1977 | Hyden et al. | 128/214 R |
| 4,223,672 | 9/1980 | Terman et al. | 128/214 R |

Primary Examiner—Dalton L. Truluck

[57] ABSTRACT

An extracorporeal method is provided for the treatment of a disease caused by pathogenic microorganisms in the bloodstream in which blood is withdrawn from a patient and at least a fraction thereof is treated with a microorganism inactivator. Then, the inactivator and any endotoxins that may be present are removed from the blood or blood fraction, and the treated blood is returned to the patient. The method may also be used to prevent the transmission of pathogenic organisms from a blood donor to a transfusion recipient.

17 Claims, 5 Drawing Figures

EXTRACORPOREAL SYSTEM FOR TREATMENT OF INFECTIOUS AND PARASITIC DISEASES

TECHNICAL FIELD

This invention relates to the extracorporeal treatment of body fluids such as blood as therapy for infectious and/or parasitic diseases characterized by the presence of pathogenic microorganisms.

BACKGROUND ART

It is known that many diseases known to human and veterinary medicine are carried by pathogenic microorganisms in the bloodstream, including viruses, Rickettsiae, bacteria, fungi, and parasitic protozoa and worms. Most of these diseases, are treated by oral ingestion or subcutaneous administration of chemical or biological drugs which destroy or deactivate the pathogenic microorganisms. However, dosages of the effective drugs must be limited because of the danger of undesirable secondary effects. Even at recommended dosages many drugs produce adverse side effects.

In addition, there are known agents which have the capacity to kill or deactivate pathogenic foreign microorganisms in vitro, but which are not used therapeutically because they are known to have toxic, or other adverse effects.

It is also known that infection is sometimes transmitted to the recipient of a whole blood or plasma transfusion from pathogenic organisms in the blood of the donor.

BRIEF SUMMARY OF THE INVENTION

In accordance with one embodiment of the present invention, undesirable microorganisms present in the bloodstream of a patient or in the blood of a blood donor are treated extracorporeally in the patient's or donor's blood, or a fraction thereof, with an inactivating agent for the microorganisms, the inactivating agent is removed prior to the blood being returned or delivered to the patient.

In one embodiment, a blood plasma fraction is treated, and the present invention provides a method of treating a patient afflicted by a microorganism-connected disease comprising withdrawing blood from said patient, separating said blood into a red cell fraction and a plasma fraction containing the microorganisms, returning said red cell fraction to said patient, treating said plasma fraction with an inactivation agent for said microorganisms, and thereafter returning said plasma fraction to said patient. The returned plasma fraction is substantially free of said microorganism inactivation agent. In another preferred embodiment, endotoxins generated by the microorganisms are also removed.

DETAILED DESCRIPTION

Figure 1:
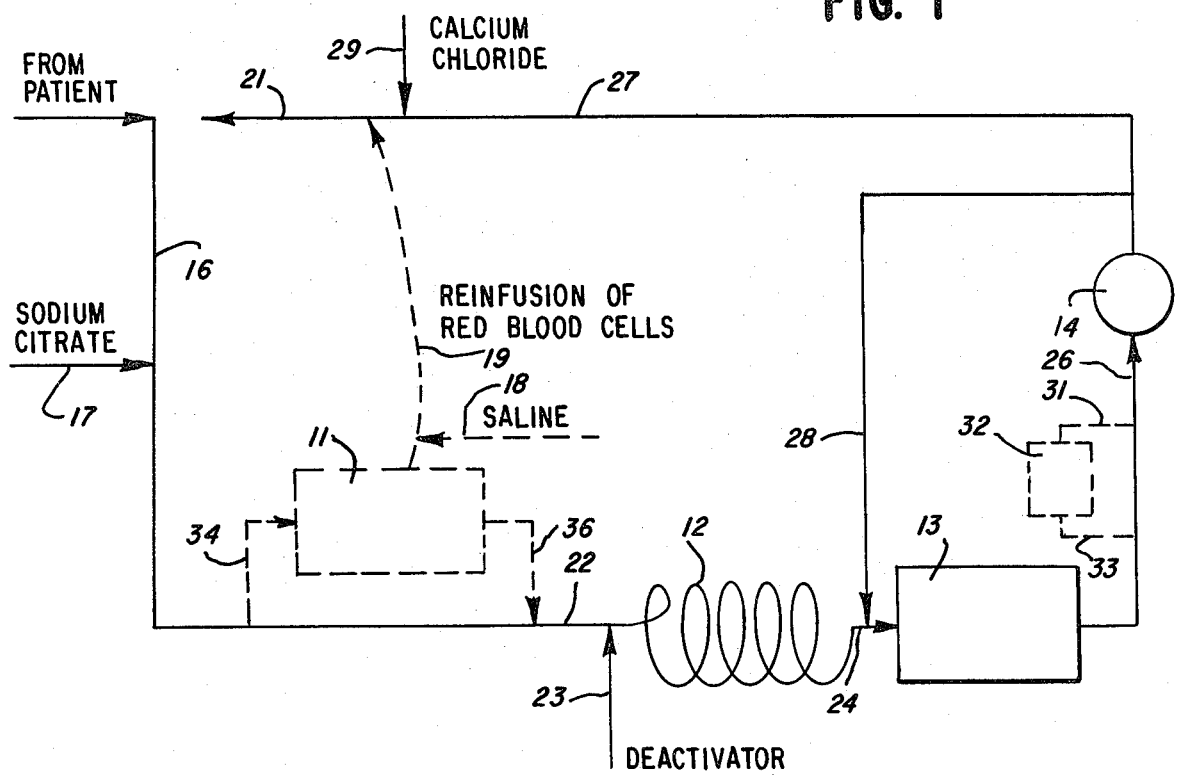
FIG. 1 shows schematically the flow and treatment of blood in accordance with the instant invention in an extracorporeal loop which includes a bioreactor.

As shown in FIG. 1, blood, withdrawn from a patient through an arterio-venous fistula (A-V fistula) or a venous puncture, is passed through line 16 and treated with an anticoagulant, e.g., a sodium citrate or heparin solution introduced through line 17.

The withdrawn blood, bearing pathogenic microorganisms, is passed through line 22 to coiled bioreactor 12. A microorganism deactivator is introduced through line 23 before the blood enters the bioreactor. The level or concentration of microorganism deactivator introduced into the blood is above physiologically acceptable levels for systemic introduction, that is, it is such that it would be harmful, or toxic, to normal body functioning if the same level were used in intracorporeal therapy.

The blood, treated with microorganism deactivator, is passed through line 24 to detoxifier 13, a dialysis unit or cell designed to remove substantially all of the microorganism deactivator from the blood. After passing through the detoxifier, the plasma fraction passes through line 26 to monitor 14, in which the microorganism deactivator level is determined.

When the microorganism deactivator level of the blood, as measured by the monitor, is below a predetermined safety limit, the blood continues in its principal cycle through line 27 for reinfusion into the bloodstream of the patient.

In the event that the microorganism deactivator level is above the predetermined safety limit after the first pass through the detoxifier, the blood is recycled through line 28 to line 24 for another pass through the detoxifier.

The dialysis taking place in detoxifier 13 removes other materials from the plasma fraction as well as the microorganism deactivator. In particular, calcium ions are removed from the plasma fraction. Inasmuch as calcium ions are essential for bone maintenance, these ions are replaced by the addition of an aqueous calcium chloride solution through line 29.

When the disease to be treated is a bacterial disease and the microorganisms to be dealt with are bacteria, there are frequently endotoxins in the bloodstream released by the dead bacteria, which are only partially removed by the dialysis in detoxifier 13. In one embodiment of the invention, an alternate path is provided through line 31, endotoxin adsorbent canister 32 and line 33, thereby eliminating substantially all of the endotoxins that are present before the treated blood is returned to line 26. The adsorbent canister contains a suitable adsorbent such as activated charcoal, crosslinked polysaccharide dextran derivatives (sold under the trademark "Sephadex"), encapsulated dolomite, protein A, immobilized antibodies and the like. In this embodiment, monitor 14 checks the endotoxin level as well as the level of microorganism deactivator; and the blood is recycled if either, or both, is at too high a level. In another embodiment, a strand or filament made of, or impregnated with, a suitable absorbent is situated within coiled bioreactor 12.

In some diseases, the microorganisms may be found substantially entirely in the blood fluid, rather than in the erythrocytes, or red blood cells, therein. Examples of such diseases are bacterial endocarditis, hepatitis, hemmorrhagic fever, bacteremias, viremias, filariasis, trypanosomiasis, and malaria in one stage of its cycle. In such cases, it may be advantageous to remove the erythrocytes from the blood to be treated to avoid possible damage to the erythrocytes at the relatively high drug levels that are utilized. In one embodiment of the invention, means is provided in membrane separator 11 for blood to be separated into a plasma fraction and an erythrocyte fraction, the blood flowing into the membrane separator through line 34 and the plasma fraction returning to line 22 through line 36.

The erythrocyte fraction, flowing in line 19 is made more fluid by the introduction of normal saline solution through line 18 and then rejoins the treated plasma in line 21 for reinfusion of whole blood into the patient.

If desired, the microorganism deactivator may be immobilized, i.e., attached to an immovable or fixed carrier instead of being added in an aqueous stream through line 23 or the deactivator may be dispensed by leaching out of a fixed carrier. In a coiled bioreactor as shown in FIG. 1, the deactivator may be attached to the interior surface of the coil or provided attached to a monofilament or strand within the coils that is spaced from the interior surface. Similarly, the endotoxin absorber may be provided on a fixed carrier within the bioreactor, as described above.

Figure 2:
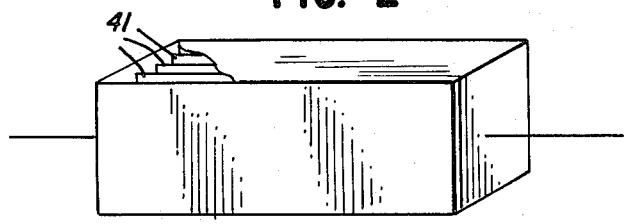
FIG. 2 is a fragmentary perspective, with a partly exposed interior, of an alternative bioreactor in the schematic flow diagram of FIG. 1.
Figure 3:
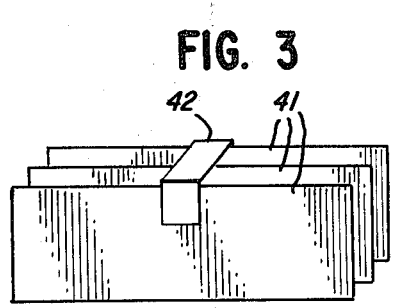
FIG. 3 is a perspective of a replaceable plate assembly utilizable within the bioreactor of FIG. 2.

The bioreactor shown in FIG. 2 is a rectangular vessel containing a spaced parallel plate assembly (shown in FIG. 3) that serves as the aforementioned fixed carrier. Each plate 41 is coated on both sides with a microorganism deactivator and/or an endotoxin absorber. The plates are held together by bridge 42. In one embodiment, the plates are coated with an intermediate layer of a binding, or holding, fibrinogen material, such as bovine agglutinin, to which the microorganism deactivator is bound.

Figure 4:
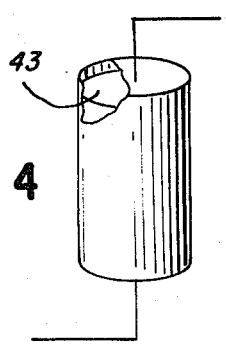
FIG. 4 is a fragmentary perspective, with a partly exposed interior, of another alternative bioreactor in the schematic diagram of FIG. 1.

The bioreactor may also comprise a packed column 43, as shown in FIG. 4, with the liquid blood, or plasma fraction passing upwardly through a pack of beads, rings, saddles or like carriers coated with a microorganism deactivator and/or endotoxin absorber.

The fixed microorganism deactivator has a limited capacity for deactivation and becomes ineffective after extended use. In the embodiments of FIGS. 2 and 4, the microorganism deactivator is easily replaced, in the FIG. 2 embodiment by a replaceable plate assembly, and in the FIG. 4 embodiment by fresh packing material. The packing material may, if desired, be replaceable as cartridge.

Figure 5:
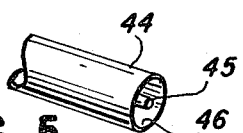
FIG. 5 is a perspective view of a segment of a bioreactor coil provided with a central monofilament or strand which serves as a carrier for a microorganism inactivator and/or endotoxin sorber.

The coiled bioreactor 12 of FIG. 1 may also be provided with a coil of the type shown in FIG. 5. In this particular embodiment coil 44 is provided with monofilament or strand 45 which serves as a carrier for the deactivator and/or endotoxin sorber. Monofilament or strand 45 may extend along the entire length of coil 44 and may be a free-floating element therewithin. Alternately, monofilament or strand 45 may be positioned spaced from coil wall 46 at a predetermined distance by means of spacers, e.g. fins, associated therewith.

In the embodiments in which the microorganism deactivator is fixed to a carrier, detoxifier 13 may be included to provide a further safety factor or it may eliminated as desired. Monitor 14 may also be eliminated in such instances, although it may, if desired, be retained as a safety feature to provide assurance against the possibility that some microorganism deactivator might become detached from its substrate. It may also serve, where necessary as a monitor for endotoxins.

In order to simplify the monitoring of microorganism inactivator, it is preferred to use a monitor that is a secondary dialysis cell and an inactivator which can be detected by its fluorescence or to add to the inactivator a compatible, dialyzable fluorescent material.

The coating of the microorganism deactivator onto a carrier such as the plates of FIG. 2 or the packing material of FIG. 4 may be effected by techniques known in the art. A suitable drug may, for example, be adhered to a glass surface through an intermediate layer of fibrinogen.

The specific microorganism deactivators used in accordance with this invention will, of course, depend on the nature of the microorganism to be dealt with. Bacterial septicemia, for example, may be associated with the proliferation in the blood stream of one or more of *Escherichia coli*, Klebsiella spp., Enterobacter spp., Meningococcus, Pneumococcus, Proteus spp., *Staphylococcus aureus* and other bacteria. In conventional septicemia therapy these microorganisms, for the most part, are killed, or otherwise inactivated in the bloodstream by oral or intravenous administration of antibiotic materials including penicillins, such as carbencillin; aminoglycosides, such as gentamicin sulfate; cephalosporins, such as cefaporazone; clindamycins, such as clindamycin hydrochloride; chloramphenicols, such as chloramphenicol palmitate; polyenes, such as ambruticin; and sulphonamides, such as cotrimoxazole. In the method of this invention, the foregoing drugs may be used in extracorporeal treatment at concentrations in the blood or plasma far in excess of accepted maximum safe concentrations for intracorporeal therapy.

Syphilis is another bacterial infection and is associated with the proliferation of *Treponema pallidum* in the blood. It is usually treated today by injection of a penicillin, such as benzathine penicillin or procaine penicillin. Erythromycin may also be used for patients sensitive to penicillin. The same drugs, in substantially higher concentrations may be used in the extracorporeal treatment of this invention. In fact, the penicillins may be used on patients sensitive to penicillin since the drug is substantially removed before the blood is returned to the patient.

Viral microorganisms associated with viremia and with viral infections accompanied by viremia, including infectious hepatitis, influenza and hemorrhagic fevers, may also be killed, or otherwise inactivated by the method of this invention. Typical antiviral agents, useful in the method of this invention, include adenosine arabinoside, imdoxuridine, ribavirine, acyclovir, and natural antiviral substances such as interferons and lymphotoxin.

Parasitic diseases, and particularly protozoal infections, such as malaria and trypanosomiasis, may also be treated by the method of this invention. One of the most effective drugs for the treatment of trypanosomiasis is melarsoprol which is a trivalent arsenical compound having substantial arsenical toxicity. By the method of this invention, however, the drug is substantially removed after the extracorporeal treatment and before return to the patient's body. Thus, substantially higher doses may be used for greater effectiveness while toxicity is minimized.

Malaria patients may be treated extracorporeally by the method of this invention with chloroquin, quinine, hydroxychloroquin, or pyrimethamine in dosages higher than those used intracorporeally. Alternatively, if the treatment can be coordinated with the chill-fever cycle to coincide with the time that the merozites of the parasite have been released from the patient's erythrocytes, the red cells may be removed before adding the microorganism deactivation agent, and recombined with the plasma after removal of the deactivation agent, as described above, to prevent damage to erythrocytes.

The invention has been described with respect to its preferred embodiments. Modifications and variations will be apparent to those skilled in the art.

I claim:

1. The method of treating or preventing a disease caused by microorganisms in the bloodstream comprising withdrawing blood from a bloodstream, treating at least a fraction of the withdrawn blood extracoporeally with a microorganism inactivator, and thereafter introducing at least a fraction of said blood, having a reduced microorganism level, into a bloodstream, said introduced blood or blood fraction being substantially free of said microorganism inactivator.

2. The method of claim 1 wherein said first named bloodstream is the same as said second named bloodstream and is the bloodstream of a patient afflicted with said disease.

3. The method of claim 1 wherein said first named bloodstream is the bloodstream of a blood donor and said second named bloodstream is the bloodstream of a transfusion recipient.

4. The method of treating a disease caused by microorganisms in the bloodstream comprising withdrawing blood from a patient, treating at least a fraction of the withdrawn blood extracorporeally with a microorganism inactivator, and thereafter returning said blood, having a reduced microorganism level, to said patient, said returning blood being substantially free of said microorganism inactivator.

5. The method of claim 4 wherein said microorganism inactivator is added to said blood or blood fraction in an aqueous medium and wherein substantially all of said microorganism inactivator is removed from said blood before said blood is returned to said patient.

6. The method of claim 5 wherein said microorganism inactivator is removed from said blood or blood fraction by dialysis.

7. The method of claim 6 wherein said blood or blood fraction is monitored by induced fluorescence to determine the level of microorganism inactivator therein after said dialysis.

8. The method of claim 4 wherein said microorganism inactivator is attached to an immovable carrier and said blood or blood fraction moves past said carrier.

9. The method of claim 8 wherein said immovable carrier comprises an inner wall of a conduit through which said blood or blood fraction is passed.

10. The method of claim 8 wherein said immovable carrier comprises a packing material in a packed column through which said blood or blood fraction is passed.

11. The method of claim 8 wherein said immovable carrier comprises an assembly of spaced parallel plates.

12. The method of claim 8 wherein said immovable carrier comprises a strand contained in the tubing of a bioreactor.

13. The method of claim 4 wherein whole blood is treated with said microorganism inactivator.

14. The method of claim 4 wherein said blood withdrawn from said patient is separated into a red cell fraction and a plasma fraction, wherein said plasma fraction is treated with said microorganism inactivator and wherein said red cell fraction and said treated plasma fraction are recombined before being returned to said patient.

15. The method of claim 4 wherein said disease is a bacterial infection and said microorganism inactivator comprises an antibiotic.

16. The method of claim 4 wherein said disease is a viral infection accompanied by viremia and said microorganism inactivator comprises an antiviral agent.

17. The method of claim 4 wherein said disease is a protozoal infection and said microorganism inactivator comprises an agent effective intracorporeally for the treatment of said disease.

* * * * *